US010863758B2

(12) United States Patent
Bedoukian

(10) Patent No.: US 10,863,758 B2
(45) Date of Patent: Dec. 15, 2020

(54) FRAGRANCE AND FLAVOR COMPOSITIONS CONTAINING ISOMERIC ALKADIENYL ESTERS

(71) Applicant: BEDOUKIAN RESEARCH, INC., Danbury, CT (US)

(72) Inventor: Matthew Bedoukian, Redding, CT (US)

(73) Assignee: BEDOUKIAN RESEARCH, INC., Danbury, CT (US)

( * ) Notice: Subject to any disclaimer, the term of this patent is extended or adjusted under 35 U.S.C. 154(b) by 0 days.

(21) Appl. No.: 15/658,940

(22) Filed: Jul. 25, 2017

(65) Prior Publication Data
US 2018/0027845 A1  Feb. 1, 2018

Related U.S. Application Data

(60) Provisional application No. 62/368,731, filed on Jul. 29, 2016.

(51) Int. Cl.

| | | |
|---|---|---|
| *A23L 2/38* | (2006.01) | |
| *C07C 69/145* | (2006.01) | |
| *C07C 69/24* | (2006.01) | |
| *C11B 9/00* | (2006.01) | |
| *A23G 4/06* | (2006.01) | |
| *A23L 2/56* | (2006.01) | |
| *C12G 3/06* | (2006.01) | |
| *A23L 27/29* | (2016.01) | |
| *C07C 69/007* | (2006.01) | |
| *A23L 27/20* | (2016.01) | |

(52) U.S. Cl.
CPC .............. *A23L 2/38* (2013.01); *A23G 4/06* (2013.01); *A23L 2/56* (2013.01); *A23L 27/202* (2016.08); *A23L 27/29* (2016.08); *C07C 69/007* (2013.01); *C07C 69/145* (2013.01); *C07C 69/24* (2013.01); *C11B 9/0019* (2013.01); *C12G 3/06* (2013.01)

(58) Field of Classification Search
CPC ..... A23L 27/202; C07C 69/007; C07C 69/24; C07C 69/145; C11B 9/0019
See application file for complete search history.

(56) References Cited

U.S. PATENT DOCUMENTS

| | | | | |
|---|---|---|---|---|
| 5,543,157 A | * | 8/1996 | Trinh ................. | A61K 47/6951 424/493 |
| 2008/0076699 A1 | | 3/2008 | Ley et al. | |
| 2010/0113837 A1 | | 5/2010 | Bedoukian et al. | |

FOREIGN PATENT DOCUMENTS

| | | | | |
|---|---|---|---|---|
| GB | 1529592 A | * | 10/1978 | ............. C07C 29/42 |
| WO | 2017100426 A1 | | 6/2017 | |

OTHER PUBLICATIONS

Adams et al. 2008. "The FEMA GRAS Assessment of α,β-unsaturated aldehydes and related substances used as flavor ingredients." Food and Chemical Toxicology. vol. 46, pp. 2935-2967.*
Kozlovskiy, M., Gobble, C., Chickos, J. 2015. "Vapor Pressures and vaporization enthalpies of a series of esters used in flavors by correlation gas chromatography." J. Chem. Thermodynamics. vol. 86, pp. 65-74.*
Smith et al. 2005. GRAS Flavoring Substances 22. Food Technology. www.ift.org. pp. 24-28, 31, 32, 34, 36, 38-62, downloaded Aug. 27, 2018.*
International Search Report and Written Opinion for the corresponding international application No. PCT/US17/43659, dated Oct. 5, 2017, 10 pages.
International Preliminary Report on Patentability for the corresponding international application No. PCT/US17/43659, dated Sep. 11, 2018, 45 pages.
Extended European Search Report for the corresponding international application No. PCT/US17/43659, dated Feb. 27, 2020, 7 pages.
Snider et al."Formal Total Synthesis of (±)-Pseudomonic Acids A and C. The Quasi-Intramolecular Lewis Acid Catalyzed Diels-Alder Reaction", Journal of Organic Chemistry Jan. 1, 1983 (48) pp. 3003-3010, American Chemical Society.

* cited by examiner

*Primary Examiner* — Nikki H. Dees
(74) *Attorney, Agent, or Firm* — Ohlandt, Greeley, Ruggiero & Perle, L.L.P.

(57) ABSTRACT

A composition containing at least one isomeric alkadienyl ester in an amount effective to impart a fragrance or flavor to the composition. A fragrance or flavor composition containing at least one isomeric alkadienyl ester in an amount effective to impart a fragrance or flavor to the composition. A consumer product containing the fragrance or flavor composition having at least one isomeric alkadienyl ester in an amount effective to impart a fragrance or flavor to the composition. A method of imparting a fragrance or flavor to a consumer product by adding to the consumer product a fragrance or flavor composition containing at least one isomeric alkadienyl ester in an amount effective to impart a fragrance or flavor to the consumer product.

24 Claims, No Drawings

FRAGRANCE AND FLAVOR COMPOSITIONS CONTAINING ISOMERIC ALKADIENYL ESTERS

RELATED APPLICATION

This application claims the benefit of U.S. Application No. 62/368,731, filed Jul. 29, 2016, which is incorporated herein by reference in its entirety.

BACKGROUND OF THE DISCLOSURE

1. Field of the Disclosure

This disclosure relates to fragrance and flavor compositions containing isomeric alkadienyl esters. This disclosure also relates to a method of imparting a fragrance or flavor to a consumer product by adding fragrance or flavor compositions containing isomeric alkadienyl esters to the consumer product.

2. Description of the Related Art

Many alkyl and alkenyl esters can be found in perfumers and flavorists' palette. For example, esters having six or more carbon atoms are known as having interesting organoleptic properties of value to the creation of fragrances and flavors.

In S. Arctander, Perfume and Flavor Chemicals, 1969, Montclair, N.J., USA, cis-4-heptenyl acetate is described as having a fresh, green, fruity odor with rose undertones whereas cis-4-heptenyl isobutyrate has grassy notes with heavy nondescript character. These esters have never achieved popularity among the users. Yet others describe the odor and taste of 2E-3,7-dimethylocta-2,6-dienyl acetate and 2Z-3,7-dimethylocta-2,6-dienyl acetate as sweet, fruity floral with dominance of rose notes.

A number of publications mention the preparation of isomers of 2,4-heptadienyl and 3,5-heptadienyl esters but there is no mention of their odor or taste properties (Snider et al J. Org. Chem. 1983, vol. 48, p. 3003-10 and Samian et al, Nauveau Journal de Chemie, 1978, 2(3), p. 249-54).

There is an ongoing interest in the fragrance and flavor industry to use new compounds that enhance or improve organoleptic character and impart new notes to help perfumers and flavorists create exciting new fragrance and flavor experience desired by consumers. There remains a need and demand for unique fragrance and flavor compositions.

The present disclosure provides many advantages, including access to novel and exciting odor and taste, which shall become apparent as described below.

SUMMARY OF THE DISCLOSURE

This disclosure relates in part to fragrance and flavor compositions containing isomeric alkadienyl esters.

This disclosure also relates in part to a composition comprising at least one isomeric alkadienyl ester in an amount effective to impart a fragrance or flavor to the composition.

This disclosure further relates in part to a consumer product containing the fragrance or flavor composition comprising at least one isomeric alkadienyl ester in an amount effective to impart a fragrance or flavor to the consumer product.

This disclosure yet further relates in part to a method of imparting a fragrance or flavor to a consumer product by adding fragrance or flavor compositions containing isomeric alkadienyl esters to the consumer product.

In accordance with this disclosure, it has been surprisingly found that heptadiene esters show a departure from the odor and taste of related known esters in having a natural, green, hyacinth, violet leaf notes dominated by fresh watery, sea weed, marine and ozonic odor and strong watermelon rind taste with fresh notes associated with many other fruits. Further, it has been surprisingly found that none of the C-7 and substituted C-8 esters with structures similar to heptadienyl esters of this disclosure had similar organoleptic properties.

Further objects, features and advantages of the present disclosure will be understood by reference to the following detailed description.

DESCRIPTION OF THE PREFERRED EMBODIMENTS

As used herein, the term "fragrance composition" refers to a mixture comprising one or more fragrance components, in any of their forms, and one or more solvents or perfuming co-ingredients. As known in the art, a fragrance composition will contain one or more fragrance components (e.g., perfuming co-ingredients) in order to impart an olfactory note to the composition (e.g., a household cleaner, perfume, or other commercial product) to which it is added. In one embodiment, the fragrance composition contains two or more fragrance components which, collectively and in combination with the solvent to which they are added, impart an intended olfactory note (e.g., a hedonically pleasing note) to a human in close proximity to the fragrance composition.

In general terms, perfuming co-ingredients belong to chemical classes as varied as alcohols, aldehydes, ketones, esters, ethers, acetates, nitriles, terpene hydrocarbons, nitrogenous or *sulphurous* heterocyclic compounds and essential oils of natural or synthetic origin, and are known to perfumers of ordinary skill in the art. Many of these ingredients are listed in reference texts such as S. Arctander, Perfume and Flavor Chemicals, 1969, Montclair, N.J., USA or any of its more recent versions, each of which are hereby incorporated by reference.

Fragrance materials and mixtures of fragrance materials which can be used in combination with the compounds according to this disclosure for manufacturing perfume compositions are, for example, natural products, such as essential oils, absolutes, resinoids, resins, concretes, etc., but also synthetic fragrance materials such as hydrocarbons, alcohols, aldehydes, ketones, ethers, acids, esters, acetals, ketals, nitriles, etc., including saturated and unsaturated compounds, aliphatic carbocyclic and heterocyclic compounds.

Examples of fragrance materials which can be used in combination with the compounds according to the disclosure include geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tertbutylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, aromatic nitromusks, and the like to mention a few.

Auxiliary substances and solvents which can be used in perfume compositions which contain compounds according to this disclosure include, for example: ethanol, isopropanol, dipropylene glycol, dipropyleneglycol monomethyl ether, diethylphthalate, and the like.

The perfumery compositions of this disclosure may be compounded according to recognized techniques of perfumery employing known odiferous perfumery ingredients, e.g., techniques and ingredients mentioned in the standard textbooks "Soap, Perfumery and Cosmetics" by W. A. Poucher, 7th edition; published by Chapman & Hall (London), 1959; "Perfume and Flavour Chemicals" by S. Arctander, published by the author (Montclair) 1959 and "Perfume and Flavour Materials of Natural Origin" also by S. Arctander, self-published, Elizabeth N.J., 1960. Specific natural odoriferous ingredients which may be blended with the materials of disclosure include vetivert oil, guaiac wood oil, lemon oil, rose absolute, jasmin absolute, geranium oil, geraniol, lanvandin oil, acetate, patchouli oil, petitgrain oil, bergamot oil, clove bud oil, bay oil, nutmeg oil, pimento berry oil, ylang oil, sandalwood oil, clary sage oil, labdamun resin, orange oil, olibanum resin, mandarin oil, neroli oil, oakmoss, cedarwood oil and many others known to perfumers.

As used herein, the term "perfume composition" refers a mixture of fragrance materials and optionally auxiliary substances, dissolved in a suitable solvent or mixed with a powdery substrate which is used to impart a desired odor to the skin and/or all types of products. Examples of such products include soaps, detergents, air fresheners, room sprays, pomanders, candles, cosmetics, such as creams, ointments, toilet waters, pre- and aftershave lotions, talcum powders, hair-care agents, body deodorants and anti-perspirants.

As used herein, the term "flavor composition" refers to a composition that contains one or more compound(s) (e.g., co-ingredients) that provide(s) a desired taste when combined with a solvent that is suitable for oral administration and oral consumption. Examples of flavoring co-ingredients that are generally included in a flavor composition are listed in S. Arctander, Perfume and Flavor Chemicals, 1969, Montclair, N.J., USA. The skilled person in the art of flavors is able to select them on the basis of its general knowledge and according to the nature of the product to be flavored and the desired taste.

In particular, the term "flavor composition" refers to a mixture of flavor materials and optionally auxiliary substances, dissolved in a suitable solvent or mixed with a powdery substrate which is used to impart a desired taste to all types of products. Examples of such products include beverages, dairy products, confectionaries, cereals, snacks, soups and the like.

As used herein, the phrase "consumer product" refers to composition that is in a form ready for use by the consumer for the marketed indication. A solvent suitable for use in a consumer product is a solvent that, when combined with other components of the end product, will not render the consumer product unfit for its intended consumer use.

Any one of the isomeric alkadienyl ester compositions of this disclosure can be included in a fragrance or flavor composition. In one embodiment, any one of the isomeric alkadienyl ester compositions of this disclosure is provided in a fragrance composition. In an alternative embodiment, any one of the isomeric alkadienyl ester compositions of this disclosure is provided in a flavor composition.

As described herein, this disclosure relates to a composition comprising at least one isomeric alkadienyl ester in an amount effective to impart a fragrance or flavor to the composition.

Also, as described herein, this disclosure relates to a fragrance or flavor comprising at least one isomeric alkadienyl ester in an amount effective to impart a fragrance or flavor to the composition.

In the composition and the fragrance or flavor composition, the at least one isomeric alkadienyl ester has from about 0.1 percent to about 99.5 percent of Z,E isomers, from about 0.1 percent to about 99.5 percent of Z,Z isomers, from about 0.1 percent to about 99.5 percent of E,E isomers, and from about 0.1 percent to about 99.5 of E,Z isomers, based on the total Z and E isomers in the composition or in the fragrance or flavor composition.

In an embodiment, in the composition and the fragrance or flavor composition, the at least one isomeric alkadienyl ester has from about 10 percent to about 98 percent of Z,E isomers, preferably from about 15 percent to about 98 percent of Z,E isomers, and more preferably from about 20 percent to about 98 percent of Z,E isomers; from about 0.5 percent to about 40 percent of Z,Z isomers, preferably from about 0.5 percent to about 38 percent of Z,Z isomers, and more preferably from about 0.5 percent to about 35 percent of Z,Z isomers; from about 0.1 percent to about 60 percent of E,E isomers, preferably from about 0.1 percent to about 38 percent of E,E isomers, and more preferably from about 0.1 percent to about 35 percent of E,E isomers; and from about 2 percent to about 40 percent of E,Z isomers, preferably from about 2 percent to about 38 percent of E,Z isomers, and more preferably from about 0.5 percent to about 35 percent of E,Z isomers; based on the total Z and E isomers in the composition or in the fragrance composition.

Further, in an embodiment, the at least one isomeric alkadienyl ester has from about 10 percent to about 98 percent of Z,E isomers, preferably from about 20 percent to about 90 percent of Z,E isomers, and more preferably from about 30 percent to about 80 percent of Z,E isomers, based on the total Z and E isomers in the composition.

Preferably, the isomeric alkadienyl esters are selected from Z,E-3,5-heptadienyl formate, Z,E-3,5-heptadienyl acetate, Z,E-3,5-heptadienyl propionate, Z,E-3,5-heptadienyl butyrate, Z,E-3,5-heptadienyl isobutyrate, Z,E-3,5-heptadienyl valerate, Z,E-3,5-heptadienyl isovalerate, Z,E-3,5-heptadienyl hexanoate, Z,E-3,5-heptadienyl benzoate, Z,E-3,5-heptadienyl lactate, Z,E-3,5-heptadienyl pyruvate, Z,E-3,5-heptadienyl salicylate, Z,E-3,5-heptadienyl tiglate, Z,E-3,5-heptadienyl methyl carbonate, Z,E-3,5-heptadienyl cis-3-hexenoate and Z,E-3,5-heptadienyl alpha methyl butyrate.

Preferred isomeric alkadienyl esters of this disclosure can be represented by the formula

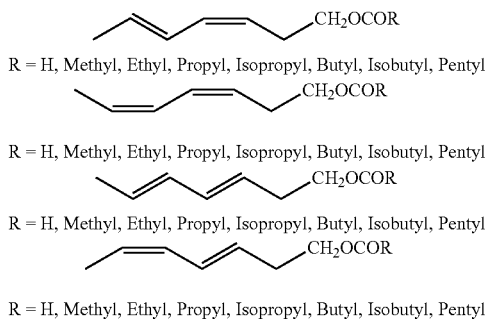

For the fragrance compositions of this disclosure, the at least one isomeric alkadienyl ester is present in an amount of at least about 1 ppm by weight, based on the total weight of the composition, to impart a fragrance to the composition.

For the flavor compositions of this disclosure, the at least one isomeric alkadienyl ester is present in an amount of at least about 0.1 ppm by weight, based on the total weight of the composition, to impart a flavor to the composition.

For the fragrance compositions of this disclosure, the at least one isomeric alkadienyl ester can be combined with geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentyl-cyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, or aromatic nitromusks, to impart a fragrance to the composition.

For the flavor compositions of this disclosure, the at least one isomeric alkadienyl ester can be combined with geraniol, geranyl acetate, linalool, linalyl acetate, citronellol, citronellyl acetate, terpineol, terpinyl acetate, 2-phenylethanol, 2-phenylethyl acetate, benzyl alcohol, benzyl acetate, benzyl salicylate, heliotropine, benzaldehyde, anisaldehyde, benzyl salicylate, e, n-decanal, n-dodecanal, 9-decen-1-ol, coumarin, eugenol, vanillin, hexanal, eucalyptol, ionones, methylionones, isomethylionones, irones, cis-3-hexenol and esters of the latter, acetaldehyde, ethyl acetate, ethyl butyratecinnamic aldehyde, cuminic aldehyde, furfural, cinnamic aldehyde, maltol, ethyl maltol, dimethyl sulfide, gamma decalactone, gamma undecalactone, diacetyl, ethyl valerate, damascone, damascenone, methyl caproate, cyclotene, butyric acid, acetoin, delta decalactone, furaneol, acetoin, benzodihydro pyrone, 2,6-nonadienal, melonal or methyl heptane carbonate, to impart a flavor to the composition.

In an embodiment, this disclosure also relates in part to the preparation of isomeric alkadienyl esters for use in fragrance and flavor formulations. These isomeric alkadienyl esters have a range of unexpected and unobvious organoleptic properties described as a natural, green, hyacinth, violet leaf notes dominated by fresh watery, sea weed, marine, ozonic, watermelon, green bell pepper etc. notes. These notes are highly desirable in creating consumer acceptable fragrances and flavors. Additionally, these isomeric alkadienyl esters are cost effective since they possess high odor intensity and can be effective at imparting the desirable organoleptic effect to a fragrance or flavor at a very low concentration.

In accordance with this disclosure, the isomeric alkadienyl esters of this disclosure can be prepared by conventional processes. The compositions of this disclosure and the fragrance compositions of this disclosure can also be prepared by conventional processes.

In an embodiment, the isomeric alkadienyl esters of this disclosure can be prepared by a process schematically represented as follows:

Step 1

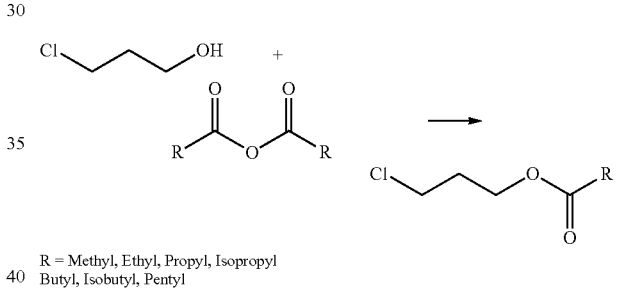

R = Methyl, Ethyl, Propyl, Isopropyl
Butyl, Isobutyl, Pentyl

Step 2

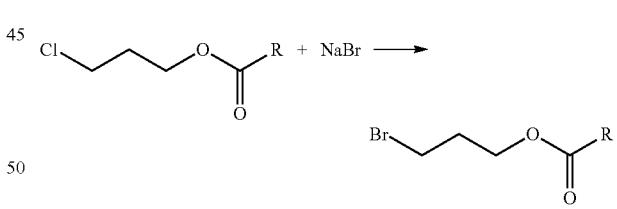

Step 3

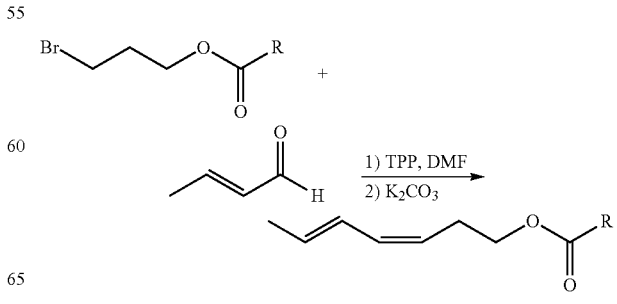

The reactions represented in the above scheme are conventional reactions described in detail in the examples herein below.

The isomeric alkadienyl esters of this disclosure have a range of natural, green, hyacinth, violet leaf notes dominated by fresh watery, sea weed, marine and ozonic notes conjuring up sea shore memories. They also have fresh, fruity, watermelon and green bell pepper notes useful in flavors.

As described herein, this disclosure provides a consumer product containing the fragrance or flavor composition comprising at least one isomeric alkadienyl ester in an amount effective to impart a fragrance or flavor to the consumer product.

As further described herein, this disclosure provides a method of imparting a fragrance or flavor to a consumer product comprising adding to the consumer product a fragrance composition comprising at least one isomeric alkadienyl ester in an amount effective to impart a fragrance or flavor to the consumer product.

Illustrative consumer fragrance products useful in this disclosure include, for example, a candle, an air care product, a perfume, a cologne, a soap, a personal care product, a detergent, a fabric care product, a household cleaning product, and the like.

More particularly, illustrative consumer fragrance products include a soap, a detergent, an air freshener, a room spray, a pomander, a candle, and a cosmetic comprising a cream, an ointment, a toilet water, a pre-shave lotion, an aftershave lotion, a talcum powder, a hair-care agent, a body deodorant, and an anti-perspirant.

Preferred illustrative consumer fragrance products include an air care product, laundry care, a perfume, and a cologne.

In an embodiment, one or more of the isomeric alkadienyl esters of the present disclosure, alone or in combination with other co-ingredients, can be employed in fragrance compositions, solvents, media and the like. As indicated herein, the use of such isomeric alkadienyl esters is applicable to a wide variety of products in the fragrance industry such as, but not limited to: candles; air fresheners; perfumes; colognes; personal care products such as soaps, deodorants, shampoos, conditioners, shower gels and shaving lotions; cosmetics such as lotions and ointments; as well as detergents; fabric care products and household cleaner/cleaning agents.

As the isomeric alkadienyl esters of the present disclosure are useful ingredients for the perfuming of various products, the present disclosure also concerns all different forms of the isomeric alkadienyl esters that can be advantageously employed in perfumery. Such forms include a composition including isomeric alkadienyl esters and a solvent commonly used in perfumery compositions. Examples of such solvents used in perfumery are known in the art and include, but are not limited to: dipropyleneglycol, diethyl phthalate, isopropyl myristate, benzyl benzoate, 2-(2-ethoxy)-1-ethanol, ethyl citrate, ethanol, water/ethanol mixtures, limonene or other terpenes, isoparaffins such as those known under the trademark Isopar™ (ExxonMobil Chemicals, Houston, Tex.), and glycol ethers and glycol ether esters such as those known under the trademark Dowanol™ (Dow Chemical Company, Midland Mich.).

The isomeric alkadienyl esters of the present disclosure are particularly valuable as being capable of imparting natural, green, hyacinth, violet leaf notes dominated by fresh watery, sea weed, marine and ozonic notes to a fragrance composition. For fragrance applications, typical concentrations of the isomeric alkadienyl esters are on the order of 0.01 ppm to 1% by weight, or more, based on the total weight of the composition into which the fragrance compound is incorporated. Those skilled in the art will be able to employ the desired level of the compounds of the disclosure to provide the desired fragrance and intensity. In general, the isomeric alkadienyl esters of the present disclosure will be used in relatively small amounts, typically via significant dilutions due to their high-impact, diffusive properties.

The perfuming compositions according to the disclosure may be in the form of a simple mixture of the various co-ingredients and solvents, or also in the form of a biphasic system such as an emulsion or microemulsion. Such systems are well-known to persons skilled in the art.

As described herein, suitable perfumed end products that can include a composition of the present disclosure including, but are not limited to: 1) candles, air fresheners, perfumes and colognes, 2) personal care products such as soaps, deodorants, shampoos, conditioners, shower gels and shaving lotions; 3) cosmetics such as lotions and ointments; as well as 4) detergents, fabric care products and household cleansers/cleaning agents. Depending on the solvents that may be present in some end products, it may be necessary to protect the isomeric alkadienyl esters from premature degradation, for example by encapsulation or with a stabilizer, or other methods well-known to those of ordinary skill in the art.

The compositions of the present disclosure can also be added to, for example: 1) fragrance products; perfume; eau de perfume; eau de toilet; eau de cologne; and the like; skin-care cosmetics, face washing creams, varnishing creams, cleansing creams, cold creams, massage creams and oils, milky lotions, skin toning lotion, cosmetic solutions, packs, makeup remover, and the like; 2) makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, and the like; 3) hair care cosmetics, pomades, brilliantines, setting lotions, hair sticks, hair solids, hair oils, hair treatments, hair creams, hair tonics, hair liquids, hair sprays, hair restorers, hair dyes, and the like; 4) sunburn cosmetics, suntan products, sunscreen products, and the like; 5) medical cosmetics, antiperspirants, after-shave lotions and gels, permanent wave lotions, medicated soaps, medicated shampoos, medicated skin care products, and the like; 6) hair care products, shampoos, rinses, shampoo-including-rinses, hair conditioners, hair treatments, hair packs, and the like; 7) as soaps, toilet soaps, bath soaps, perfumed soaps, transparent soaps, synthetic soaps, and the like; 8) body washing soaps, body soaps, body shampoos, hand soaps, and the like; 9) bathing, bathing agents (e.g., bath salts, bath tablets, bath liquids, and the like), foam baths (bubble bath and the like), bath oils (e.g., bath perfumes, bath capsules and the like), milk baths, bath gels, bath cubes, and the like; 10) detergents, heavy duty detergents for clothes, light duty detergents for clothes, liquid detergents, laundering soaps, compact detergents, powder soaps, and the like; 11) softening finishing agents, softeners, furniture care products, and the like; and deodorants, aromatic substances and the like; and 12) insect repellent, insecticides, and the like.

Fragrances in consumer products provide several functions. They mask base odors, provide aesthetic pleasure and signal product attributes and function to the user, e.g., hygiene, cleanliness, mildness. Notwithstanding these benefits, it is also true that perfumes can cause a myriad of problems within products they have been added to, e.g., discoloration, phase separation, problems such as irritation and occasional allergic reaction to the user. Additionally, fragrances represent one of the more expensive components of the product and many fragrance ingredients may not be easily biodegradable. Over the years, perfume levels in many consumer products have increased by the popular demand but at the same time consumers have also become more critical of the fragranced products they purchase and use.

Therefore, in an embodiment, this disclosure provides high intensity consumer acceptable fragrances and desirable hedonics at a much lower concentration than achieved before. This lowering of fragrance concentration in consumer products by an order of magnitude has the benefit of cost saving, less interference with the physical properties of the product base, minimizing toxicological implications on the user, and lowering the environmental impact of chemicals used.

The quantities in which the compositions of this disclosure can be used in perfume compositions or in products to be perfumed can vary within wide limits and depend inter alia on the nature of the product in which the fragrance material is used, on the nature and quantity of the other components in the perfume composition and on the odor effect which is aimed at. It is therefore only possible to specify very rough limits, which, however, provide sufficient information for the specialist to be able to use the compounds according to the disclosure independently. In most cases a quantity of only 1 ppm in a perfume composition will already be sufficient to obtain a clearly perceptible odor effect. On the other hand, to achieve special odoriferous effects it is possible to use quantities of 100, 1000, 5000 ppm or even more in a composition. In products perfumed with such compositions, these concentrations are proportionately lower, depending on the quantity of composition used in the product.

There are three basic stages of a fragrance. The first stage (i.e., top notes) is the first impression that a fragrance gives to a customer. This initial stage is the most volatile. In the second stage (i.e., middle notes), a few moments after the application of a fragrance, the heart is revealed. This modifying part of the fragrance has medium volatility. In the third stage (i.e., base notes), after a fragrance dries down, these notes are more pronounced. This part of the fragrance is the longest lasting. The balance between these three groups is very important. In a well-balanced fragrance, it is important to understand what group or groups are the most important for a particular application. The fragrance compositions of this disclosure exemplify a desirable balance between these three groups for desired applications.

Illustrative consumer flavor products useful in this disclosure include, for example, a beverage, a powder or semi-frozen/frozen concentrate for a drink, a candy, a sugarless candy, a chocolate, a chewing gum, a bubble gum, a condiment, a spice, a seasoning, a dry cereal, an oatmeal, a granola bar, an alcoholic beverage, an energy beverage, a juice, a tea, a coffee, a salsa, a gel bead, a film strip for halitosis, a lozenge, a cough drop, a throat lozenge, a throat spray, a toothpaste, and a mouth rinse.

More particularly, illustrative consumer flavor products include a beverage, a dairy product, a confectionary, a cereal, a snack, and a soup.

Preferred illustrative consumer flavor products include a beverage, a chewing gum, and a bubble gum.

In an embodiment, one or more of the isomeric alkadienyl esters of the present disclosure, alone or in combination with other co-ingredients, can be employed in fragrance and flavor compositions, solvents, media and the like. As indicated herein, the use of such isomeric alkadienyl esters is applicable to a wide variety of products in the fragrance industry such as, but not limited to: candles; air fresheners; perfumes; colognes; personal care products such as soaps, deodorants, shampoos, conditioners, shower gels and shaving lotions; cosmetics such as lotions and ointments; as well as detergents; fabric care products and household cleaner/cleaning agents. Also, as indicated herein, the use of such isomeric alkadienyl esters is also applicable to a wide variety of products in the flavor industry such as, but not limited to: foodstuffs such as baked goods, dairy products, desserts, etc.; beverages such as juices, sodas, teas, flavored waters, fruit-based "smoothy" drinks, milk-based drinks, etc.; confectionaries such as sweets, hard candy, gums; and gelatinous materials, snacks, desserts, pharmaceuticals, oral care products and the like.

As the isomeric alkadienyl esters of the present disclosure are useful ingredients for the perfuming or flavoring of various products, the present disclosure also concerns all different forms of the isomeric alkadienyl esters that can be advantageously employed in perfumery or in flavors. Such forms include a composition including isomeric alkadienyl esters and a solvent commonly used in perfumery or in flavor compositions. Examples of such solvents used in perfumery are known in the art and include, but are not limited to: dipropyleneglycol, diethyl phthalate, isopropyl myristate, benzyl benzoate, 2-(2-ethoxy)-1-ethanol, ethyl citrate, ethanol, water/ethanol mixtures, limonene or other terpenes, isoparaffins such as those known under the trademark Isopar™ (ExxonMobil Chemicals, Houston, Tex.), and glycol ethers and glycol ether esters such as those known under the trademark Dowanol™ (Dow Chemical Company, Midland Mich.). Examples of solvents commonly used in flavors are also known in the art and include, but are not limited to: propylene glycol, triacetin, triethyl citrate, benzyl alcohol, benzyl benzoate, ethanol, vegetable oils and terpenes.

The isomeric alkadienyl esters of the present disclosure are particularly valuable as being capable of imparting natural, green, hyacinth, violet leaf notes dominated by fresh watery, sea weed, marine and ozonic notes to a fragrance composition. For example, z,e-3,5-heptadienyl acetate can be used to impart a natural, green, violet leaf, floral, ozonic, marine characteristic to fragrance compositions. For fragrance applications, typical concentrations of the isomeric alkadienyl esters are on the order of 0.01 ppm to 1% by weight, or more, based on the total weight of the composition into which the fragrance compound is incorporated. Those skilled in the art will be able to employ the desired level of the compounds of the disclosure to provide the desired fragrance/flavor intensity. In general, the isomeric alkadienyl esters of the present disclosure will be used in relatively small amounts, typically via significant dilutions due to their high-impact, diffusive properties.

The perfuming compositions according to the disclosure may be in the form of a simple mixture of the various co-ingredients and solvents, or also in the form of a biphasic system such as an emulsion or microemulsion. Such systems are well-known to persons skilled in the art.

As described herein, suitable perfumed end products that can include a composition of the present disclosure including, but are not limited to: 1) candles, air fresheners, perfumes and colognes, 2) personal care products such as soaps, deodorants, shampoos, conditioners, shower gels and shaving lotions; 3) cosmetics such as lotions and ointments; as well as 4) detergents, fabric care products and household cleansers/cleaning agents. Depending on the solvents that may be present in some end products, it may be necessary to protect the isomeric alkadienyl esters from premature degradation, for example by encapsulation or with a stabilizer, or other methods well-known to those of ordinary skill in the art.

The compositions of the present disclosure can also be added to, for example: 1) fragrance products; perfume; eau de perfume; eau de toilet; eau de cologne; and the like; skin-care cosmetics, face washing creams, varnishing creams, cleansing creams, cold creams, massage creams and oils, milky lotions, skin toning lotion, cosmetic solutions, packs, makeup remover, and the like; 2) makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, and the like; 3) hair care cosmetics, pomades, brilliantines, setting lotions, hair sticks, hair solids, hair oils, hair treatments, hair creams, hair tonics, hair liquids, hair sprays, hair restorers, hair dyes, and the like; 4) sunburn cosmetics, suntan products, sunscreen products, and the like; 5) medical cosmetics, antiperspirants, after-shave lotions and gels, permanent wave lotions, medicated soaps, medicated shampoos, medicated skin care products, and the like; 6) hair care products, shampoos, rinses, shampoo-including-rinses, hair conditioners, hair treatments, hair packs, and the like; 7) as soaps, toilet soaps, bath soaps, perfumed soaps, transparent soaps, synthetic soaps, and the like; 8) body washing soaps, body soaps, body shampoos, hand soaps, and the like; 9) bathing, bathing agents (e.g., bath salts, bath tablets, bath liquids, and the like), foam baths (bubble bath and the like), bath oils (e.g., bath perfumes, bath capsules and the like), milk baths, bath gels, bath cubes, and the like; 10) detergents, heavy duty detergents for clothes, light duty detergents for clothes, liquid detergents, laundering soaps, compact detergents, powder soaps, and the like; 11) softening finishing agents, softeners, furniture care products, and the like; and deodorants, aromatic substances and the like; 12) insect repellent, insecticides, and the like; 13) oral care products such as tooth pastes, mouth cleaners, mouth wash, troches, chewing gums, and the like; and 14) pharmaceutical products, poultices, external skin care pharmaceuticals such as ointments, internal administration medicines, and the like.

Furthermore, the compositions of the disclosure, in any of their forms, can also be incorporated into flavoring compositions or flavored products, together with co-ingredients or adjuvants, e.g., to impart fresh, fruity, watermelon and green bell pepper taste to flavoring compositions, foods or beverages. Consequently, the use of the compositions of the present disclosure, in any of their forms, as flavoring ingredients, is another object of the present disclosure, as is a flavor composition comprising an isomeric alkadienyl esters of the present disclosure.

The flavor compositions according to the disclosure may be in the form of a simple mixture of flavoring ingredients or in an encapsulated form, e.g., a flavoring composition entrapped into a solid matrix that may comprise wall-forming and plasticizing materials such as mono-, di- or trisaccharides, natural or modified starches, hydrocolloids, cellulose derivatives, polyvinyl acetates, polyvinylalcohols, proteins or pectins. Examples of particularly useful matrix materials include, for example, sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylinethyl cellulose, derivatives, gelatin, agar, alginate and mixtures thereof. Encapsulation is well-known to persons skilled in the art, and may be performed, for instance, using techniques such as spray-drying, agglomeration or extrusion, or coating encapsulation, including coacervation and complex coacervation techniques.

The compositions of the present disclosure are particularly valuable as being capable of imparting tropical, berry, bakery, caramel, watermelon, and vegetable notes, to flavor ingredients. Specifically, z,e-3,5-heptadienyl propionate and isobutyrate can be used to impart a strawberry and watermelon characteristic to flavor compositions respectively. For flavor applications, typical concentrations of isomeric alkadienyl esters are of the order of 0.1 ppb-100 ppm. Preferably, applicable concentrations fall in the range of 0.001 ppm-0.01 ppm. Those skilled in the art will be able to employ the desired level of the isomeric alkadienyl esters to provide the desired flavor and intensity. Much higher concentrations may be employed when the compounds are used in concentrated flavors and flavor compositions.

In an embodiment, a composition of the present disclosure is used in chewing and bubble gums and confectionaries (e.g., hard or soft candies or lozenges). Chewing gum compositions typically include one or more gum bases and other standard components such as flavoring agents, softeners, sweeteners and the like. Flavoring agents for use in chewing gum compositions are well known and include natural flavors such as citrus oils, peppermint oil, spearmint oil, oil of wintergreen, natural menthol, cinnamon, ginger and the like; artificial flavors such as menthol, carvone, limonene, cinnamic aldehyde, linalool, geraniol, ethyl butyrate, and the like. As is known in the art, the ingredients used in chewing gum compositions can include sweeteners, both natural and artificial and both sugar and sugarless. Sweeteners are typically present in the chewing gum compositions in amounts of from about 20% to 80% by weight, preferably from about 30% to 60% by weight, based on the total weight of the chewing gum composition. Sugarless sweeteners include, but are not limited sugar alcohols such as Sorbitol, manifold, xylitol, hydrogenated starch hydrolysates, malitol and the like. High intensity sweeteners such as sucralose, aspartame, neotame, salts of acesulfame, and the like, when employed, are typically present up to about 1.0% by weight.

In an alternative embodiment, a composition of the present disclosure is included in an oral personal care product (e.g., a mouthwash or toothpaste). For example, a mouthwash can be prepared by dissolving a flavor composition (e.g., a flavor cocktail) (liquid or powder) that includes a composition of the present disclosure in a solvent (e.g., water) that further includes, for example, a flavor such as menthol and a surfactant; and then mixing the resulting solution with, for example, an aqueous erythritol solution.

In one embodiment of the present disclosure, a composition of the present disclosure is added, directly or indirectly, to a pharmaceutical dosage form (e.g., a tablet, capsule, drop or lozenge) that contains a therapeutically active agent (e.g., a medicament). For example, one embodiment of the present disclosure provides a cough drop or lozenge containing one or more compositions of the present disclosure and, optionally, further containing menthol or other medicaments for the treatment of sore throat, coughing or other upper respiratory ailments.

One or more of the present compositions can also be added to, for example, compositions for the preparation of:

1) carbonated or non-carbonated fruit beverages, carbonated cola drinks, wine coolers, fruit liquors, cordials, milk drinks, smoothy drinks, flavored water, tropical alcoholic and "virgin" drink mixes (e.g. margarita, pina colada or "rum-runner" concentrates), and powders for drinks (e.g., powdered sports or "hydrating" drinks); 2) frozen confectioneries such as ice creams, sherbets, and ice-lollies, hard candies, soft candies, taffies, chocolates, and sugarless candies; 3) desserts such as jelly and pudding; 4) confectioneries such as cakes, cookies, chewing gums and bubble gums; 5) condiments, spices and seasonings, dry cereals, oatmeals, and granola bars; 6) alcoholic beverages, energy beverages, juices, teas, coffees, salsa, and gel beads; 7) film strips for halitosis, and oral personal care products; 8) gelatin candies, pectin candies, starch candies, lozenges, cough drops, throat lozenges, throat sprays, and toothpastes.

The present compositions may also be added to, for example; 1) confectioneries such as buns with jam filling, and bars of sweet jellied paste; 2) jams; candies; 3) breads; 4) beverages such as green tea, oolong tea, black tea, persimmon leaf tea, Chamomile tea, Sasa *veitchii* tea, mulberry leaf tea, Houttuynia *cordata* tea, Puer tea, Mate tea, Rooibos tea, Gimunema tea, Guava tea, coffee, espresso, and hot and cold espresso and coffee products obtained by mixing espresso and/or coffee with milk, water or other liquids suitable for oral consumption (e.g., lattes, cafe au lait, cafe mocha) and cocoa; 5) soups such as Japanese flavor soup, western flavor soup, and Chinese flavor soup; 6) seasonings; 7) various instant beverages and foods; 8) various snack foods; and 9) other compositions for oral use.

As described herein, the compositions of this disclosure can be used in a broad range of fragrance and flavor applications, e.g., fine fragrances, household products, laundry products, personal care products and cosmetics. The flavor use can be in foodstuffs such as soups, beverages, dairy products, confectionaries, cereals, snack, etc. These compositions can be employed in widely varying amounts, depending upon the specific application and on the nature and amounts of other odor or taste carrying ingredients. But because of the exceptional strength of these compositions, the effect can be achieved at a very low level of incorporation.

While we have shown and described several embodiments in accordance with our disclosure, it is to be clearly understood that the same may be susceptible to numerous changes apparent to one skilled in the art. Therefore, we do not wish to be limited to the details shown and described but intend to show all changes and modifications that come within the scope of the appended claims.

The following examples are only to illustrate the preparation and use of the compounds according to the disclosure. The disclosure is not limited thereto.

Example 1

Preparation of Z,E-3,5-Heptadienol

Step 1—Preparation of 3-Chloropropanyl Butyrate 3-chloropropanol (1 kg) was charged to a reactor and then heated to 120° C. followed by the gradual addition of butyric anhydride (1.75 kg) maintaining a temperature of 120-130° C. Allowed to stir for 10 minutes at temperature once feed is complete and then strip out as much butyric acid as possible without co-distilling product with the help of an appropriate column. The reaction product was allowed to cool down to room temperature and then washed with 10% sodium carbonate solution until the aqueous layer was basic. Stripped the product to remove any moisture and used in the next step.

Step 2—Preparation of 3-Bromopropanyl Butyrate

3-Chloropropanyl butyrate (1 kg) was charged to a reactor to which was added sodium bromide (0.937 kg) and dimethylformamide (500 g). The reaction mixture was heated to 120-125° C. until conversion to bromide was over 60%. The reaction mixture was cooled then worked up with water. The aqueous layer was extracted with cyclohexane. The reaction mixture was stripped then distilled to separate the chloride from the bromide. Object was to achieve 95% bromide before moving to the next step.

Step 3—Preparation of Z,E-3,5-Heptadienyl Butyrate

Triphenylphosphine (1.324 kg) and DMF (1.29 kg) were charged to the reactor and contents were heated to 90-95° C. Slowly added 3-bromopropyl butyrate controlling slightly exothermic reaction. Stirred at 95-100° C. over approximately 16 hours. Once bromide had reacted, the reactor was cooled to 50-60° C. and then added potassium carbonate (1.01 kg). Heated contents to 100° C. and then added over 2-4 hours crotonal (0.335 kg). Stirred for 1 hour. The reaction mixture was cooled to below 50° C. and then quenched with water (4.9 litres). The aqueous layer was extracted with heptane. Dried and distilled over to obtain Z,E-3,5-heptadienyl butyrate.

Step 4—Preparation of Z,E-3,5-Heptadienol

To the reactor added methanol (0.13 kg) and 45% solution of potassium hydroxide (0.72 kg). Heated contents to 55° C. and then added 3,5-heptadienyl butyrate (1.0 kg). The exothermic reaction was maintained in 55° C.–70° C. range. Once the hydrolysis is complete wash with 2.0 litre of water twice. Extract with cyclohexane (2×0.28 kg). Strip solvent and pullover the product. The Z,E-3,5-heptadienol from this process was used to make acetate, propionate, butyrate and isobutyrate esters by methods known to the industry.

Example 2

Preparation of Fragrance Formulation Containing Z,E-3,5-Heptadienyl Acetate

The following perfume composition was formulated using Z,E-3,5-heptadienyl acetate in an appropriate quantity to provide fresh, ozonic, watery, sweet fruity, floral notes to the fragrance composition.

| PEACH BLOSSOM—102 | |
| --- | --- |
| Benzaldehyde 10% | 20 |
| Citronellyl Iso Butyrate | 5 |
| Linalyl Iso Butyrate | 5 |
| Damascone Delta 1% | 50 |
| Decalactone Delta | 40 |
| Decalactone Gamma | 40 |
| DPG | 353 |
| Ethyl Aceto Acetate | 10 |
| Ethyl Butyrate 1% | 10 |
| Galaxolide 50 DPG | 150 |
| Hexenal, trans-2 1% | 10 |
| Hexenol, trans-2 1% | 40 |

-continued

| PEACH BLOSSOM—102 | |
|---|---|
| Isoamyl Butyrate 1% | 3 |
| Isopropyl-4-Methylthiazol-2 1% | 40 |
| Linalol | 100 |
| Mandarin Ald 1% | 10 |
| P-Menthene-8-Thiol 0.1% | 12 |
| Terpineol | 30 |
| Triplal | 10 |
| Undecalactone Gamma | 50 |
| Apritone | 2 |
| z,e-3,5 -Heptadienyl Acetate | 10 |
| Total | 1000 |

Example 3

Preparation of Fragrance Formulation Containing Z,E-3,5-Heptadienyl Butyrate

The following perfume composition was formulated using Z,E-3,5-heptadienyl butyrate to impart fresh, green, watery, and fruity floral notes.

Topical Breeze—4

| Allyl Caproate | 105 |
|---|---|
| Allyl Heptoate | 75 |
| Amyl Cinn Ald | 7.5 |
| Benz Acetate | 7.5 |
| Coumarin | 7.5 |
| Davana Oil | 15 |
| Ethyl Aceto Acetate | 30 |
| Ethyl Caproate | 9 |
| Ethyl Caprylate | 27 |
| Linalol | 38 |
| Maltol | 3 |
| Mandarin Oil | 30 |
| Octalactone Gamma | 2 |
| Orange Oil | 226 |
| Orange Terpenes | 45 |
| Undecalactone Gamma | 15 |
| Tangerine Oil | 76 |
| Terpineol | 3 |
| Vanillin | 7.5 |
| DPG | 261 |
| z,e-3,5-Heptadienyl Butyrate | 10 |
| | 1000 |

Example 4

Preparation of Strawberry Flavor Formulation Containing Z,E-3,5-Heptadienyl Propionate The following flavor composition was formulated using Z,E-3,5-heptadienyl propionate to impart fresh, tropical, fruity, green notes.

| 2-Methyl-2-Pentenoic Acid | 0.30 |
|---|---|
| Acetic Acid | 3.00 |
| Acetoin | 0.20 |
| Aldehyde C-14 | 1.00 |
| Butyric Acid | 0.30 |
| Caproic Acid | 1.00 |
| Cis-3-Hexenol | 0.30 |
| Cis-3-Hexenyl Acetate | 0.10 |
| Ethyl Acetate | 2.00 |
| Ethyl Acetoacetate | 3.00 |
| Ethyl Butyrate | 5.00 |
| Ethyl Caproate | 1.00 |
| Gamma Decalactone | 3.00 |
| Styrallyl Acetate | 0.30 |
| Isoamyl Isovalerate | 0.10 |
| Isovaleric Acid | 0.30 |
| Methyl Octine Carbonate | 0.10 |
| Trans-2-Hexenal | 0.10 |
| Propylene Glycol | 78.90 |
| Total | 100.00 |

Flavored water was prepared by adding 200 ppm of sucralose 25% solution and 400 ppm citric acid 50% solution followed by 0.05% strawberry flavor concentrate (above) and 5 ppm of Z,E-3,5-heptadienyl propionate. The formulation with and without the heptadienyl propionate was tested by an expert panel. The flavored water containing Z,E-3,5-heptadienyl propionate was unanimously preferred over the sample without.

Example 5

Preparation of Watermelon Flavor Formulation Containing Z,E-3,5-Heptadienyl Isobutyrate The following flavor composition was formulated using Z,E-3,5-heptadienyl isobutyrate to add fresh and strong watermelon mixed with other fruity notes.

| Ethyl Maltol | 0.60 |
|---|---|
| Cis-3-Hexenol (1.00%) | 0.15 |
| 2,6-Nonadienal (10.00%) | 0.10 |
| Trans-2-Hexenal (10.00%) | 0.10 |
| Benzaldehyde | 0.10 |
| Ethyl Acetate | 1.50 |
| Ethyl Butyrate | 2.30 |
| Melonal | 1.00 |
| Alpha Ionone | 0.40 |
| Methyl Heptine Carbonate (10.00%) | 0.60 |
| Propylene Glycol | 92.70 |
| Total | 100.00 |

Flavored water was prepared by adding 200 ppm of sucralose 25% solution followed by 25 ppm watermelon flavor concentrate (above) and 5 ppm of Z,E-3,5-heptadienyl isobutyrate. The formulation with and without the heptadienyl isobutyrate was tested by an expert panel. The flavored water containing Z,E-3,5-heptadienyl isobutyrate was unanimously preferred over the sample without.

The present disclosure is not to be limited in scope by the specific embodiments described herein. Indeed, various modifications of the disclosure in addition to those described herein will become apparent to those skilled in the art from the foregoing description. Such modifications are intended to fall within the scope of the appended claims.

What is claimed is:

1. A composition comprising at least one isomeric 3,5-heptadienyl ester in an amount effective to impart a fragrance or flavor to the composition; wherein the at least one isomeric 3,5-heptadienyl ester is selected from the group consisting of 3,5-heptadienyl acetate, 3,5-heptadienyl propionate, 3,5-heptadienyl butyrate, 3,5-heptadienyl isobutyrate, 3,5-heptadienyl tiglate, and 3,5-heptadienyl alpha methyl butyrate; wherein the at least one isomeric 3,5- heptadienyl ester has from about 70 percent to about 99.5 percent of Z,E isomers, and from about 0.1 percent to about 30 percent of E,E isomers, based on the total Z and E isomers in the composition; wherein the at least one isomeric 3,5-heptadienyl ester imparts a fragrance selected from the group consisting of at least one of natural, green, sweet, fruity, floral, fresh, watery, sea weed, marine, and ozonic notes, to the composition; or wherein the at least one isomeric 3,5-heptadienyl ester imparts a flavor selected from the group consisting of at least one of fresh, tropical, green, fruity, watermelon, berry, bakery, caramel, vegetable, and green bell pepper notes, to the composition.

2. The composition of claim 1 wherein the at least one isomeric 3,5-heptadienyl ester is Z,E-3,5-heptadienyl acetate, Z,E-3,5-heptadienyl propionate, Z,E-3,5-heptadienyl butyrate, Z,E-3,5-heptadienyl isobutyrate, Z,E-3,5-heptadienyl tiglate, or Z,E-3,5-heptadienyl alpha methyl butyrate.

3. A fragrance or flavor composition comprising at least one isomeric 3,5-heptadienyl ester in an amount effective to impart a fragrance or flavor to the composition; wherein the at least one isomeric 3,5-heptadienyl ester is selected from the group consisting of 3,5-heptadienyl acetate, 3,5-heptadienyl propionate, 3,5-heptadienyl butyrate, 3,5-heptadienyl isobutyrate, 3,5-heptadienyl tiglate, and 3,5-heptadienyl alpha methyl butyrate; wherein the at least one isomeric 3,5-heptadienyl ester has from about 70 percent to about 99.5 percent of Z,E isomers, and from about 0.1 percent to about 30 percent of E,E isomers, based on the total Z and E isomers in the composition; wherein the at least one isomeric 3,5-heptadienyl ester imparts a fragrance selected from the group consisting of at least one of natural, green, sweet, fruity, floral, fresh, watery, sea weed, marine, and ozonic notes, to the fragrance composition; or wherein the at least one isomeric 3,5-heptadienyl ester imparts a flavor selected from the group consisting of at least one of fresh, tropical, green, fruity, berry, bakery, caramel, vegetable, and green bell pepper notes, to the flavor composition.

4. The fragrance or flavor composition of claim 3 wherein the at least one isomeric 3,5-heptadienyl ester is Z,E-3,5-heptadienyl acetate, Z,E-3,5-heptadienyl propionate, Z,E-3,5-heptadienyl butyrate, Z,E-3,5-heptadienyl isobutyrate, 3,5-heptadienyl tiglate, or Z,E-3,5-heptadienyl alpha methyl butyrate.

5. A consumer product containing the fragrance or flavor composition of claim 3.

6. The consumer product of claim 5 selected from the group consisting of a candle, an air care product, a perfume, a cologne, a soap, a personal care product, a detergent, a fabric care product, and a household cleaning product.

7. The consumer product of claim 5 selected from the group consisting of a soap, a detergent, an air freshener, a room spray, a pomander, a candle, and a cosmetic comprising a cream, an ointment, a toilet water, a pre-shave lotion, an aftershave lotion, a talcum powder, a hair-care agent, a body deodorant, and an anti-perspirant.

8. The consumer product of claim 5 selected from the group consisting of an air care product, a perfume, and a cologne.

9. The consumer product of claim 5 selected from the group consisting of a beverage, a powder or semi-frozen/frozen concentrate for a drink, a candy, a sugarless candy, a chocolate, a chewing gum, a bubble gum, a condiment, a spice, a seasoning, a dry cereal, an oatmeal, a granola bar, an alcoholic beverage, an energy beverage, a juice, a tea, a coffee, a salsa, a gel bead, a film strip for halitosis, a lozenge, a cough drop, a throat lozenge, a throat spray, a toothpaste, and a mouth rinse.

10. The consumer product of claim 5 selected from the group consisting of a beverage, a dairy product, a confectionary, a cereal, a snack, and a soup.

11. The consumer product of claim 5 selected from the group consisting of a beverage, a chewing gum, and a bubble gum.

12. A method of imparting a fragrance or flavor to a consumer product comprising adding to the consumer product the fragrance or flavor composition of claim 3 in an amount effective to impart a fragrance or flavor to the consumer product.

13. A composition comprising at least one isomeric 3,5-heptadienyl ester in an amount effective to impart a fragrance or flavor to the composition; wherein the at least one isomeric 3,5-heptadienyl ester is selected from the group consisting of Z,E-3,5-heptadienyl acetate, Z,E-3,5-heptadienyl propionate, Z,E-3,5-heptadienyl butyrate, Z,E-3,5-heptadienyl isobutyrate, 3,5-heptadienyl tiglate, and Z,E-3,5-heptadienyl alpha methyl butyrate, wherein the at least one isomeric 3,5-heptadienyl ester has from about 70 percent to about 99.5 percent of Z,E isomers, based on the total Z and E isomers in the composition; wherein the at least one isomeric 3,5-heptadienyl ester imparts a fragrance selected from the group consisting of at least one of natural, green, sweet, fruity, floral, fresh, watery, sea weed, marine, and ozonic notes, to the composition; or wherein the at least one isomeric 3,5-heptadienyl ester imparts a flavor selected from the group consisting of at least one of fresh, tropical, green, fruity, watermelon, berry, bakery, caramel, vegetable, and green bell pepper notes to the composition.

14. The composition of claim 13 wherein the at least one isomeric 3,5-heptadienyl ester is present in an amount of at least about 1 ppm by weight, based on the total weight of the composition, to impart a fragrance to the composition.

15. The composition of claim 13 wherein the at least one isomeric 3,5-heptadienyl ester is combined with geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentyl-cyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, ironed, cis-3-hexenol and esters of the latter, indan-musks, tetraline-musks, isochromane-musks, macrocyclic ketones, macrolactone-musks, ethylene brassylate, or aromatic nitromusks, to impart a fragrance to the composition.

16. The composition of claim 13 wherein the at least one isomeric 3,5-heptadienyl ester is present in an amount from about 0.01 ppm to about 1% by weight, based on the total weight of the composition, to impart a fragrance to the composition.

17. The composition of claim 13 wherein the at least one isomeric 3,5-heptadienyl ester is present in an amount from about 0.1 ppb to about 100 ppm by weight, based on the total weight of the composition, to impart a flavor to the composition.

18. The composition of claim 13 wherein the at least one isomeric 3,5-heptadienyl ester imparts a fragrance of natural, green, hyacinth, violet leaf notes dominated by fresh watery, sea weed, marine or ozonic notes to the composition; or wherein the at least one isomeric 3,5-heptadienyl ester imparts a flavor of fresh, fruity, watermelon or green bell pepper notes to the composition.

19. A fragrance or flavor composition comprising at least one isomeric 3,5-heptadienyl ester in an amount effective to impart a fragrance or flavor to the composition; wherein the at least one isomeric 3,5-heptadienyl ester is selected from the group consisting of Z,E-3,5-heptadienyl acetate, Z,E-3,5-heptadienyl propionate, Z,E-3,5-heptadienyl butyrate, Z,E-3,5-heptadienyl isobutyrate, 3,5-heptadienyl tiglate, and Z,E-3,5-heptadienyl alpha methyl butyrate; wherein the at least one isomeric 3,5-heptadienyl ester has from about 70 percent to about 99.5 percent of Z,E isomers, based on the total Z and E isomers in the composition; wherein the at least one isomeric 3,5-heptadienyl ester imparts a fragrance selected from the group consisting of at least one of natural, green, sweet, fruity, floral, fresh, watery, sea weed, marine, and ozonic notes, to the fragrance composition; or wherein the at least one isomeric 3,5-heptadienyl ester imparts a flavor selected from the group consisting of at least one of fresh, tropical, green, fruity, watermelon, berry, bakery, caramel, vegetable, and green bell pepper notes, to the flavor composition.

20. The fragrance or flavor composition of claim 19 wherein the at least one isomeric 3,5-heptadienyl ester is present in an amount of at least about 1 ppm by weight, based on the total weight of the composition, to impart a fragrance or flavor to the composition.

21. The fragrance or flavor composition of claim 19 wherein the at least one isomeric 3,5-heptadienyl ester is combined with geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, or aromatic nitromusks, to impart a fragrance to the composition.

22. The fragrance or flavor composition of claim 19 wherein the at least one isomeric 3,5-heptadienyl ester is present in an amount from about 0.01 ppm to about 1% by weight, based on the total weight of the composition, to impart a fragrance to the composition.

23. The fragrance or flavor composition of claim 19 wherein the at least one isomeric 3,5-heptadienyl ester is present in an amount from about 0.1 ppb to about 100 ppm by weight, based on the total weight of the composition, to impart a flavor to the composition.

24. The fragrance or flavor composition of claim 19 wherein the at least one isomeric 3,5-heptadienyl ester imparts a fragrance of natural, green, hyacinth, violet leaf notes dominated by fresh watery, sea weed, marine or ozonic notes to the composition; or wherein the at least one isomeric 3,5-heptadienyl ester imparts a flavor of fresh, fruity, watermelon or green bell pepper notes to the composition.

* * * * *